US006746856B2

(12) United States Patent
Cawley et al.

(10) Patent No.: US 6,746,856 B2
(45) Date of Patent: Jun. 8, 2004

(54) MICROBIAL CONVERSION OF BICYCLIC HETEROAROMATIC COMPOUNDS

(75) Inventors: James J. Cawley, Lyme, CT (US); John W. Wong, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/924,292

(22) Filed: Aug. 8, 2001

(65) Prior Publication Data

US 2002/0045225 A1 Apr. 18, 2002

Related U.S. Application Data

(60) Provisional application No. 60/224,089, filed on Aug. 9, 2000.

(51) Int. Cl.[7] .............................. C12P 17/00; C12N 1/00; C12N 1/14
(52) U.S. Cl. .................... 435/117; 435/243; 435/254.1; 435/254.3; 435/254.5
(58) Field of Search ................................ 435/117, 243, 435/254.1, 254.3, 254.5

(56) References Cited

U.S. PATENT DOCUMENTS

| | | | |
|---|---|---|---|
| 4,859,592 A | 8/1989 | Hagedorn et al. | 435/122 |
| 5,104,798 A | 4/1992 | Kiener | 435/117 |
| 5,213,973 A | 5/1993 | Hoeks | 435/117 |
| 5,236,832 A | 8/1993 | Kiener | 435/117 |
| 6,361,979 B1 * | 3/2002 | Burns et al. | 435/119 |

FOREIGN PATENT DOCUMENTS

| | | |
|---|---|---|
| WO | WO9639385 | 12/1996 |
| WO | WO9940061 | 8/1999 |

OTHER PUBLICATIONS

G. M. Gaucher, et al., Symposium: Antibiotics, Chapter 15, pp. 219–232, "The Initiation and Longevity of Patulin Biosynthesis".

Harayama, S. et al., *J. Bacteriol.*, vol. 167 (2), pp. 455–461 (1986).

Keiner, A., *Angew. Chem. Int. Ed. Engl.*, vol. 31 (6), pp. 774–775 (1992).

* cited by examiner

*Primary Examiner*—Christopher R. Tate
*Assistant Examiner*—Kailash C. Srivastava
(74) *Attorney, Agent, or Firm*—Peter C. Richardson; Gregg C. Benson; Christine S. Lee

(57) ABSTRACT

The present invention relates to processes for the microbial oxidation of bicyclic heteroaromatic compounds which comprise contacting these compounds with a microorganism, or a suitable mutant thereof, and incubating the resulting mixture under conditions sufficient to yield an amount of their respective carboxylic acids. The present processes optionally further comprise the isolation and purification of the product carboxylic acids.

4 Claims, No Drawings

MICROBIAL CONVERSION OF BICYCLIC HETEROAROMATIC COMPOUNDS

CROSSREFERENCE TO RELATED APPLICATION

This application claims priority from U.S. Provisional Patent Application No. 60/224,089 filed Aug. 9, 2000, the benefit of which is hereby claimed under 37 C.F.R. §1.78(a)(3).

FIELD OF THE INVENTION

The present invention relates to novel processes for preparing the carboxylic acids of bicyclic heteroaromatic compounds and, more specifically, relates to the microbial oxidation of 2-methylquinoline to 2-quinolinecarboxylic acid, 3-methylquinoline to 3-quinolinecarboxylic acid, 8-methylquinoline to 8-quinolinecarboxylic acid, 3-methylisoquinoline to 3-isoquinolinecarboxylic acid, 2-methylindole to 2-indolecarboxylic acid, and 5-chloro-2-methylindole to 5-chloro-2-indolecarboxylic acid.

BACKGROUND OF THE INVENTION

Methods are known in the art for microbial oxidation of certain aromatic heterocycles and, in particular, for microbial oxidation of methyl groups on certain aromatic heterocycles, such as, for example, those described in the following two articles and patent: (a) "Gene Order of the TOL Catabolic Plasmid Upper Pathway Operon and Oxidation of Both Toluene and Benzyl Alcohol by the xy/A Product," by S. Harayama et al., *J. Bacteriol.,* 167(2): 455–461 (1986), (b) "Enzymatic Oxidation of Methyl Groups on Aromatic Heterocycles: A Versatile Method for the Preparation of Heteroaromatic Carboxylic Acids," by A. Keiner, *Angew. Chem. Int. Ed. Engl.,* 31(6): 774–775 (1992), and (c) U.S. Pat. No. 4,859,592 (a microbial process for the production of picolinic acid).

"The Initiation and Longevity of Patulin Biosynthesis," by Gaucher et al. as published in *Dev. Ind. Microbiol.,* 22: 219–232 (1981), describes that the fungus *Penicillium griseofulvum* contains three enzymes for the conversion of m-cresol to m-hydroxybenzoic acid: m-cresol methyl hydroxylase, m-hydroxybenzyl alcohol dehydrogenase and m-hydroxybenzaldehyde hydroxylase.

As described earlier with reference to the aforementioned article by Harayama et al., the TOL plasmid pWWO of *P. putida* mt-2 is a transmissible extrachromosomal element which encodes all of the enzymes required for the oxidative catabolism of several aromatic hydrocarbons, including toluene, m-xylene and p-xylene. Bacteria carrying TOL plasmids, e.g., *P. putida* ATCC No. 33015, can convert certain aromatic hydrocarbons to their corresponding aromatic carboxylic acids: both the xyl operon which codes for enzymes of xylene degradation and the genes which are responsible for the regulation of the xyl gene lie on the TOL plasmid pWWO. The genes on the TOL plasmid pWWO which code for the enzymes required for the above oxidations must be induced to produce such enzymes.

U.S. Pat. Nos. 5,104,798; 5,213,973; and 5,236,832 disclose a microbial process for the oxidation of methyl groups in certain aromatic 5- or 6-member ring heterocycles to the corresponding carboxylic acids which is performed by a bacterium of the species Pseudomonas, the strain *P. putida* ATCC No. 33015, utilizing toluene, xylene or cymene as the inducer.

U.S. patent application Ser. No. 09/492,548 ("the '548 application") filed Jan. 27, 2000, and claiming priority from U.S. Provisional Patent Application No. 60/119,942 filed on Feb. 12, 1999, discloses microbial processes for substantially oxidizing 2-methylquinoxaline to 2-quinoxalinecarboxylic acid. In addition, the processes of the '548 application allow for suitable recovery of the 2-quinoxalinecarboxylic acid. As mentioned therein, U.S. Provisional Patent Application No. 60/073,801 ("the '801 application") filed Feb. 5, 1998, now International PCT Application No. PCT/IB99/00067 filed Jan. 18, 1999, and published on Aug. 12, 1999 as WO99/40061, discloses the use of 2-quinoxalinecarboxylic acid as an intermediate in the synthesis of novel dihydroxyhexanoic acids which are useful to treat, e.g., inflammation and other immune disorders. The 2-quinoxalinecarboxylic acid provided by the novel processes of the '548 application can be used to synthesize such dihydroxyhexanoic acids.

To reiterate, as is known in the art, certain fungi and bacteria contain enzymes for the oxidation of methyl groups on certain aromatic rings to their corresponding carboxylic acids. While it is known then that methyl groups on such heteroaromatic rings can be oxidized to their corresponding carboxylic acids using microorganisms, as would be appreciated by those skilled in the art, the chemical and optical yields of such microbial oxidations generally vary substantially depending on, for example, the particular microorganism chosen, the concentration of the substrate, the structure of the substrate, and the like.

It has now been found that a range of microorganisms, including fungi and bacteria, and suitable mutants thereof, oxidize certain bicyclic heteroaromatic compounds to an amount of their corresponding carboxylic acids, and that these carboxylic acids so generated can be suitably recovered.

The 5-chloro-2-indolecarboxylic acid provided by the novel processes of the present invention can be used to synthesize indole-2-carboxamides disclosed in International PCT Application No. PCT/IB95/00443 ("the '443 application) filed Jun. 6, 1995, and published on Dec. 12, 1996 as WO96/39385, which can be used, e.g., as inhibitors of glycogen phosphorylase, and to treat, e.g., glycogen phosphorylase-dependent diseases or conditions.

All of the documents cited herein, including the foregoing, are incorporated by reference herein in their entireties.

SUMMARY OF THE INVENTION

The present invention relates to microbiological processes for preparing the carboxylic acids of bicyclic heteroaromatic compounds.

The present invention relates to microbiological processes for preparing the compound of Formula I

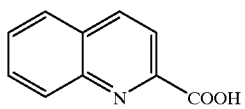

by contacting the compound of Formula II

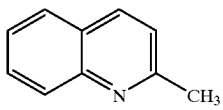

with a microorganism capable of accomplishing the oxidation of the methyl group of the compound of Formula II to the carboxyl group of the compound of Formula I, and incubating the resultant mixture under suitable conditions to yield an amount of the compound of Formula I.

The present invention also relates to microbiological processes for preparing the compound of Formula III

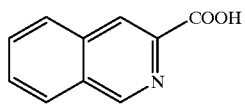

by contacting the compound of Formula IV

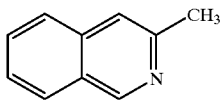

with a microorganism capable of accomplishing the oxidation of the methyl group of the compound of Formula IV to the carboxyl group of the compound of Formula III, and incubating the resultant mixture under suitable conditions to yield an amount of the compound of Formula III.

The present invention also relates to microbiological processes for preparing the compound of Formula V

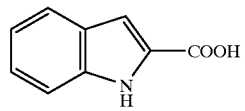

by contacting the compound of Formula VI

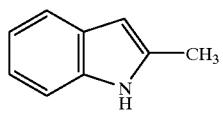

with a microorganism capable of accomplishing the oxidation of the methyl group of the compound of Formula VI to the carboxyl group of the compound of Formula V, and incubating the resultant mixture under suitable conditions to yield an amount of the compound of Formula V.

The present invention also relates to microbiological processes for preparing the compound of Formula VII

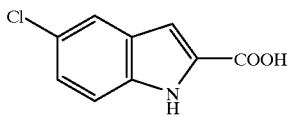

by contacting the compound of Formula VIII

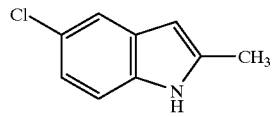

with a microorganism capable of accomplishing the oxidation of the methyl group of the compound of Formula VII to the carboxyl group of the compound of Formula V, and incubating the resultant mixture under suitable conditions to yield an amount of the compound of Formula VII.

The present invention further relates to microbiological processes for preparing the compound of Formula IX

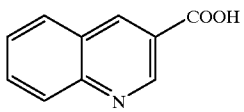

by contacting the compound of Formula X

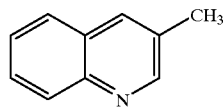

with a microorganism capable of accomplishing the oxidation of the methyl group of the compound of Formula X to the carboxyl group of the compound of Formula IX, and incubating the resultant mixture under suitable conditions to yield an amount of the compound of Formula IX.

The present invention further yet relates to microbiological processes for preparing the compound of Formula XI

by contacting the compound of Formula XII

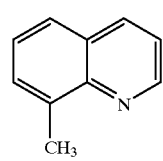

with a microorganism capable of accomplishing the oxidation of the methyl group of the compound of Formula XII to the carboxyl group of the compound of Formula XI, and incubating the resultant mixture under suitable conditions to yield an amount of the compound of Formula XI.

Accordingly, the present invention provides processes for carrying out the microbial oxidation of the compound of Formula II, 2-methylquinoline, which comprises:

contacting the compound of Formula II with a microorganism, or a mutant thereof which is known or otherwise obtainable by those skilled in the relevant art and able, despite such mutation, to accomplish the subject oxidation ("a suitable mutant thereof"), and incubating the resulting mixture under conditions sufficient to yield an amount of the compound of Formula I, wherein said microorganism is selected from the group consisting of *Cunninghamella echinulata* ATCC No. 9244, *Cunninghamella echinulata* ATCC No. 8688a, *Cunninghamella echinulata* ATCC No. 26269, *Cunninghamella echinulata* ATCC No. 8983, *Cunninghamella echinulata* ATCC No. 10028b, *Cunninghamella echinulata* ATCC No. 9245, *Cunninghamella echinulata* ATCC No. 36112, *Cunninghamella homothallica* ATCC No. 16161, *Alternaria solani* ATCC No. 11078, *Penicillium glabrum* ATCC No. 11080, *Diplodia gossypina* ATCC No. 20575, *Absidia repens* ATCC No. 14849, *Absidia repens* ATCC No. 74481, *Aspergillus tamarii* ATCC No. 16865, and *Glomerella lagenaria* ATCC No. 14724; and suitable mutants thereof.

The present invention also provides processes for carrying out the microbial oxidation of the compound of Formula IV, 3-methylisoquinoline, which comprises:

contacting the compound of Formula IV with a microorganism, or a mutant thereof which is known or otherwise obtainable by those skilled in the relevant art and able, despite such mutation, to accomplish the subject oxidation ("a suitable mutant thereof"), and incubating the resulting mixture under conditions sufficient to yield an amount of the compound of Formula III, 3-isoquinolinecarboxylic acid, wherein said microorganism is selected from the group consisting of *Cunninghamella echinulata* ATCC No. 9244, *Cunninghamella echinulata* ATCC No. 8688a, *Cunninghamella echinulata* ATCC No. 26269, *Cunninghamella echinulata* ATCC No. 8983, *Cunninghamella echinulata* ATCC No. 10028b, *Cunninghamella echinulata* ATCC No. 9245, *Cunninghamella echinulata* ATCC No. 36112, *Cunninghamella homothallica* ATCC No. 16161, *Alternaria solani* ATCC No. 11078, *Penicillium glabrum* ATCC No. 11080, *Diplodia gossypina* ATCC No. 20575, *Absidia repens* ATCC No. 14849, *Absidia repens* ATCC No. 74481, *Aspergillus tamarii* ATCC No. 16865, *Glomerella lagenaria* ATCC No. 14724, *Rhodococcus rhodochrous* ATCC No. 19067, *Pseudomonas putida* ATCC No. 33015 and *Pseudomonas putida* ATCC No. 202190; and suitable mutants thereof;

provided that where said microorganism is said *Pseudomonas putida* ATCC No. 33015 or said *Pseudomonas putida* ATCC No. 202190, said *Pseudomonas putida* ATCC No. 33015 or said *Pseudomonas putida* ATCC No. 202190 is induced by interaction with an inducer prior to said contacting of said *Pseudomonas putida* ATCC No. 33015 or said *Pseudomonas putida* ATCC No. 202190 with said 3-methylisoquinoline.

The present invention further provides processes for carrying out the microbial oxidation of the compound of Formula VI, 2-methylindole, which comprises:

contacting the compound of Formula VI with a microorganism, or a mutant thereof which is known or otherwise obtainable by those skilled in the relevant art and able, despite such mutation, to accomplish the subject oxidation ("a suitable mutant thereof"), and incubating the resulting mixture under conditions sufficient to yield an amount of the compound of Formula V, 2-indolecarboxylic acid, wherein said microorganism is selected from the group consisting of *Cunninghamella echinulata* ATCC No. 8688a, *Cunninghamella echinulata* ATCC No. 8983, *Cunninghamella echinulata* ATCC No. 10028b, and *Rhodococcus rhodochrous* ATCC No. 19067; and suitable mutants thereof.

The present invention also provides processes for carrying out the microbial oxidation of the compound of Formula VIII, 5-chloro-2-methylindole, which comprises:

contacting the compound of Formula VIII with a microorganism, or a mutant thereof which is known or otherwise obtainable by those skilled in the relevant art and able, despite such mutation, to accomplish the subject oxidation ("a suitable mutant thereof"), and incubating the resulting mixture under conditions sufficient to yield an amount of the compound of Formula VII, 5-chloro-2-indolecarboxylic acid, wherein said microorganism is selected from the group consisting of *Cunninghamella echinulata* ATCC No. 9244, *Cunninghamella echinulata* ATCC No. 8688a, *Cunninghamella echinulata* ATCC No. 26269, *Cunninghamella echinulata* ATCC No. 8983, *Cunninghamella echinulata* ATCC No. 10028b, *Cunninghamella echinulata* ATCC No. 9245, *Cunninghamella echinulata* ATCC No. 36112, *Cunninghamella homothallica* ATCC No. 16161, *Alternaria solani* ATCC No. 11078, *Penicillium glabrum* ATCC No. 11080, *Diplodia gossypina* ATCC No. 20575, *Absidia repens* ATCC No. 14849, *Absidia repens* ATCC No. 74481, *Glomerella lagenaria* ATCC No. 14724, *Rhodococcus rhodochrous* ATCC No. 19067; and suitable mutants thereof.

The present invention also provides processes for carrying out the microbial oxidation of the compound of Formula IX, 3-methylquinoline, which comprises:

contacting the compound of Formula X with a microorganism, or a mutant thereof which is known or otherwise obtainable by those skilled in the relevant art and able, despite such mutation, to accomplish the subject oxidation ("a suitable mutant thereof"), and incubating the resulting mixture under conditions sufficient to yield an amount of the compound of Formula IX, 3-quinolinecarboxylic acid, wherein said microorganism is selected from the group consisting of *Pseudomonas putida* ATCC No. 33015 and *Pseudomonas putida* ATCC No. 202190; and suitable mutants thereof;

provided that said microorganism is induced by interaction with an inducer prior to said contacting of said microorganism with said 3-methylquinoline.

The present invention also provides processes for carrying out the microbial oxidation of the compound of Formula XI, 8-methylquinoline, which comprises:

contacting the compound of Formula XII with a microorganism, or a mutant thereof which is known or otherwise obtainable by those skilled in the relevant art and able, despite such mutation, to accomplish the subject oxidation ("a suitable mutant thereof"), and incubating the resulting mixture under conditions sufficient to yield an amount of the compound of Formula XII, 8-quinolinecarboxylic acid, wherein said microorganism is selected from the group consisting of *Pseudomonas putida* ATCC No. 33015 and *Pseudomonas putida* ATCC No. 202190; and suitable mutants thereof;

provided that said microorganism is induced by interaction with an inducer prior to said contacting of said microorganism with said 8-methylquinoline.

The subject processes optionally further comprise the isolation of the desired product, specifically, 2-quinoxalinecarboxylic acid, 3-isoquinolinecarboxylic acid, 2-indolecarboxylic acid, 5-chloro-2-indolecarboxylic acid, 3-quinolinecarboxylic acid, and 8-quinolinecarboxylic acid, by any suitable method. For example, the reaction mixture can be extracted with an organic solvent, preferably, ethyl acetate, and then the extracted material can be chromatographed. Alternatively, the product carboxylic acid can be adsorbed from the reaction mixture onto a resin, preferably a polymeric adsorbent resin, eluted therefrom using an organic solvent, preferably ethyl acetate, and crystallized from the eluted material using an organic solvent, or a combination of organic solvents, preferably ethyl acetate and methanol. Further yet, the carboxylic acids produced by the present processes may be treated with a suitable base, e.g., sodium hydroxide, resulting in the formation of a salt, e.g., sodium salt, of e.g., 2-quinoxalinecarboxylic acid. The alkali salt of the carboxylic acids produced by the present processes can then be isolated from the bioconversion medium by removal of the cells from the medium by filtration or centrifugation, followed by concentration of the cell-free medium, e.g., by evaporation.

The subject microorganism is preferably an intact microorganism.

In a preferred embodiment of the present invention wherein the substrate is 2-methylquinoline, the microorganism is a fungus which is selected from the group consisting of the genera Cunninghamella, Alternaria, Penicillium, and Diplodia, but the species thereof is not particularly limitative provided that the microorganisms, or mutants thereof, are capable of accomplishing the subject oxidations.

In a particularly preferred embodiment of the present invention wherein the substrate is 2-methylquinoline, the microorganism is a fungus which is selected from the group consisting of *Cunninghamella echinulata* ATCC No. 9244, *Cunninghamella echinulata* ATCC No. 8688a, *Cunninghamella echinulata* ATCC No. 26269, *Cunninghamella echinulata* ATCC No. 8983, *Cunninghamella echinulata* ATCC No. 10028b, *Cunninghamella echinulata* ATCC No. 9245, *Cunninghamella echinulata* ATCC No. 36112, *Cunninghamella homothallica* ATCC No. 16161, *Alternaria solani* ATCC No. 11078, *Penicillium glabrum* ATCC No. 11080, and *Diplodia gossypina* ATCC No. 20575; and suitable mutants thereof, or, further yet, any deposit of these microorganisms, or suitable mutants thereof, made to comply with the terms of the Budapest Treaty.

In an especially preferred embodiment of the present invention wherein the substrate is 2-methylquinoline, the microorganism is a fungus which is selected from the group consisting of *Cunninghamella echinulata* ATCC No. 9244, *Cunninghamella echinulata* ATCC No. 8688a, *Cunninghamella echinulata* ATCC No. 26269, *Cunninghamella echinulata* ATCC No. 8983, *Cunninghamella echinulata* ATCC No. 10028b, *Cunninghamella echinulata* ATCC No. 9245, and *Cunninghamella echinulata* ATCC No. 36112; and suitable mutants thereof.

In a preferred embodiment of the present invention wherein the substrate is 3-methylisoquinoline, the microorganism is a fungus which is selected from the group consisting of the genera Cunninghamella, Alternaria, Penicillium, Diplodia, Aspergillus, and Glomerella, but the species thereof is not particularly limitative provided that the microorganisms, or mutants thereof, are capable of accomplishing the subject oxidations.

In a particularly preferred embodiment of the present invention wherein the substrate is 3-methylisoquinoline, the microorganism is a fungus which is selected from the group consisting of *Cunninghamella echinulata* ATCC No. 8688a, *Alternaria solani* ATCC No. 11078, *Diplodia gossypina* ATCC No. 20575, *Aspergillus tamarii* ATCC No. 16865 and *Glomerella lagennaria* ATCC No. 14724; and suitable mutants thereof, or, further yet, any deposit of these microorganisms, or suitable mutants thereof, made to comply with the terms of the Budapest Treaty.

In an especially preferred embodiment of the present invention wherein the substrate is 3-methylisoquinoline, the microorganism is *Aspergillus tamarii* ATCC No. 16865 and suitable mutants thereof.

In another preferred embodiment of the present invention wherein the substrate is 3-methylisoquinoline, the microorganism is wherein said microorganism is selected from the group consisting of *Pseudomonas putida* ATCC No. 33015 and *Pseudomonas putida* ATCC No. 202190; and suitable mutants thereof, or, further yet, any deposit of these microorganisms, or suitable mutants thereof, made to comply with the terms of the Budapest Treaty.

In a preferred embodiment of the present invention wherein the substrate is 2-methylindole, the microorganism is a bacterium.

In a particularly preferred embodiment of the present invention wherein the substrate is 2-methylindole, the microorganism is *Rhodococcus rhodochrous* ATCC No. 19067 and suitable mutants thereof, or, further yet, any deposit of these microorganisms, or suitable mutants thereof, made to comply with the terms of the Budapest Treaty.

In a preferred embodiment of the present invention wherein the substrate is 5-chloro-2-methylindole, the microorganism is a bacterium.

In a particularly preferred embodiment of the present invention wherein the substrate is 5-chloro-2-methylindole, the microorganism is *Rhodococcus rhodochrous* ATCC No. 19067 and suitable mutants thereof, or, further yet, any deposit of these microorganisms, or suitable mutants thereof, made to comply with the terms of the Budapest Treaty.

A preferred cell density for the fungal cultures of the present invention is from about 10 to about 30 g dry cell weight/L.

In another preferred embodiment of the present invention the microorganism is a bacterium.

A preferred cell density for the bacterial cultures of the present invention is a density which gives an optical density of from about 10 to about 50 at 650 nm.

As discussed above, in embodiments of the present invention wherein the microorganism is *Pseudomonas putida* ATCC No. 33015 or *Pseudomonas putida* ATCC No. 202190, or a suitable mutant thereof, the microorganism, or suitable mutant thereof, is induced prior to or during the contacting. It is preferred that the contacting occur after the completion of the induction of the microorganism. Preferred inducers include p-xylene, m-xylene, benzyl alcohol, 2-chlorotoluene, and 2-bromotoluene. Particularly preferred inducers include p-xylene and benzyl alcohol.

In a preferred embodiment of the present invention wherein the microorganism is *Pseudomonas putida* ATCC No. 33015 or *Pseudomonas putida* ATCC No. 202190, or a suitable mutant thereof, and the microorganism is cultured in a growth medium in a flask, the inducer is added to such growth medium prior to or along with the contacting of the microorganism with the substrate, specifically 3-methylquinoline, 3-methylisoquinoline, or 8-methylquinoline, and incubated in such growth medium for a period of time sufficient for the substantial completion of such induction. The cells of the induced microorganism are collected by centrifuging the contents of the flask, removing, e.g., decanting, the spent growth medium (and thus the subject inducer), washing the cell pellet and resuspending the pellet in an aqueous medium, such as DPBS (Biowhittaker), prior to the contacting of said substrate with said microorganism.

In another preferred embodiment of the present invention wherein the microorganism is *Pseudomonas putida* ATCC No. 33015 or *Pseudomonas putida* ATCC No. 202190, or a suitable mutant thereof, and the subject microorganism is cultured in a growth medium in a fermentor, the inducer is continuously or continually added to such growth medium prior to the subject contacting of the microorganism with the substrate and incubated in such growth medium for a period of time sufficient for the substantial completion of such induction, and then discontinued prior to the contacting of said substrate with said microorganism.

In another preferred embodiment of the present invention wherein the microorganism is *Pseudomonas putida* ATCC No. 33015 or *Pseudomonas putida* ATCC No. 202190, or a suitable mutant thereof, and the subject microorganism is cultured in a growth medium in a fermentor, the inducer is continuously or continually added to such growth medium prior to the subject contacting of the microorganism with the substrate and incubated in such growth medium for a period of time sufficient for the substantial completion of such induction, and then continued along with the contacting of said substrate with said microorganism.

In a further preferred embodiment of the present invention the subject contacting is accomplished by adding the substrate to a growth medium comprising the subject microorganism where the microorganism is a fungus. In a preferred embodiment of the present invention wherein the subject contacting is accomplished by adding the substrate to a growth medium comprising the subject fungus, the growth medium is cornsteep solids medium. A particularly preferred cornsteep solids medium comprises from about 20 g to about 40 g/liter cornsteep solids and about 20 g/L dextrose, having a pH of about pH 4.85. Another preferred growth medium comprises about 20 g/L Pharmamedia® (Traders Protein) and about 20 g/L dextrose, having a pH of about pH 7.2.

In yet another preferred embodiment of the present invention the contacting is by adding the substrate, e.g., the compound of Formula II, adsorbed to a resin. See, for example, the article by J. T. Vicenzi et al., "Large-scale stereoselective enzymatic ketone reduction with in situ product removal via polymeric adsorbent resins," *Enzyme and Microbial Technology*, 20: 494–499 (1997).

In still another preferred embodiment of the present invention the contacting is accomplished by adding the substrate to an aqueous medium comprising washed cells of the microorganism.

In yet another preferred embodiment of the present invention the microorganism is washed prior to the contacting of the microorganism with the substrate. In a preferred embodiment of the present invention wherein the microorganism is washed prior to the contacting of the microorganism with the substrate the washed microorganism is immobilized prior to the contacting.

In another preferred embodiment of the present invention the microorganism is grown in a cornsteep solids medium for from about twenty-four hours to about seventy-two hours prior to the contacting which is accomplished by adding the substrate thereto.

The processes of the present invention further optionally comprise the isolation or separation of the product carboxylic acid, e.g., carried out by extraction with organic solvent, adsorption onto a resin, crystallization, or, as discussed above, where the alkali salt of the product carboxylic acid is provided, by concentration by evaporation of a cell-free medium, or the like.

The present invention further includes the use of 5-chloro-2-indolecarboxylic acid in the synthesis of the novel indole-2-carboxamides disclosed in the aforementioned '443 application by following any of the methods disclosed in the '443 application or by using any other suitable methods therefor.

Those skilled in the art will fully understand the terms used herein to describe the present invention; nonetheless, the following terms used herein are as described immediately below.

"Intact microorganism" means that the cells of the microorganism substantially possess their inherent (and/or induced, as the case may be) mechanical, physical and biochemical integrities.

"Microbial oxidation" means the oxidation of the present invention as accomplished by the intact microorganism, or any suitable preparation thereof, and the like.

"Microorganism" includes any intact microorganism or suitable preparation therefrom, including, for example, microorganism washed free of, e.g., fermentation medium, growth medium, culture broth, and the like, as the case may be; and microorganism immobilized, e.g., in a column, attached to beads, and the like.

DETAILED DESCRIPTION OF THE INVENTION

Unless otherwise noted, throughout this specification and the appendant claims: ° C. is degrees Centigrade; % is percent; ACN is acetonitrile; DMSO is dimethylsulfoxide; DPBS is Dulbeccos phosphate buffered saline; EtOAC is ethyl acetate; EtOH is ethanol; g is gram; HPLC is high performance liquid chromatography; L is liter; MeOH is methanol; mg is milligram; min is minute or minutes; mm is millimeter; mmol is millimoles; mL is milliliter; m-xylene is meta-xylene; N is normal (concentration); nM is nanomolar (concentration); PBS is phosphate buffered saline; p-xylene is para-xylene; rpm is revolutions per minute; TFA is trifluoroacetic acid; $\mu$L is microliter; v/v is volume per volume; and American National Can® is located in Menasha, Wis., U.S.A.; Becton Dickinson® Labware is located in Franklin Lakes, N.J., U.S.A.; Becton Dickinson® Microbiology Systems, Sparks, Md., U.S.A.; Biowhittaker® is located in Walkersville, Md., U.S.A.; Column Engineering®, Inc. is located in Ontario, Calif., U.S.A.; IEC® Centrifuge is located in Needham Heights, Mass., U.S.A.; Rohm and Haas® is located in Philadelphia, Pa., U.S.A.; and Traders Protein® is located in Memphis, Tenn., U.S.A.

Further, ATCC is American Type Culture Collection which is located at 10801 University Boulevard, Manassas, Va., 20110-2209, U.S.A. TABLE 1 below lists the microorganisms disclosed herein and their depositor(s) (see, www.ATCC.com).

TABLE 1

| Fungal Culture, ATCC No. | Depositor |
|---|---|
| *Absidia repens*, 14849 | NRRL[1] |
| *Absidia repens*, 74481 | Pfizer Inc.[2] |
| *Alternaria solani*, 11078 | P. W. Brian |
| *Aspergillus tamarii*, 16865 | K. B. Raper, D. I. Fennell |
| *Cunninghamella echinulata*, 8688a | NRRL |
| *Cunninghamella echinulata*, 8983 | V. M. Cutter, Jr. |
| *Cunninghamella echinulata*, 9244 | V. M. Cutter, Jr. |
| *Cunninghamella echinulata*, 9245 | V. M. Cutter, Jr. |
| *Cunninghamella echinulata*, 10028b | NRRL |
| *Cunninghamella echinulata*, 26269 | J. J. Perry |
| *Cunninghamella echinulata*, 36112 | J. J. Perry |
| *Cunninghamella homothallica*, 16161 | IFO-Institute for Fermentation |

TABLE 1-continued

| | Depositor |
|---|---|
| *Diplodia gossypina*, 20575 | Hoffman-La Roche Ltd. |
| *Glomerella lagenaria*, 14724 | Sanraku-Ocean Co., Ltd. |
| *Penicillium glabrum*, 11080 | P. W. Brian |
| Bacterial Culture, ATCC No. | |
| *Pseudomonas putida*, 33015 | P. A. Williams |
| *Pseudomonas putida*, 202190 | Pfizer Inc.[3] |
| *Rhodococcus rhodochrous*, 19067 | J. W. Foster | wherein: [1]NRRL is Northern Regional Research Laboratories (Peoria, Illinois);
[2]*A. repens*, 14849, deposited under the terms of the Budapest Treaty on January 13, 1999; and
[3]*P. putida*, 33015, deposited under the terms of the Budapest Treaty on January 13, 1999.

The processes of the present invention are readily carried out. The microorganism is cultivated, with induction where necessary, e.g., where the microorganism is *Pseudomonas putida* ATCC No. 33015 or *Pseudomonas putida* ATCC No. 202190, or a suitable mutant thereof, and then contacted with the substrate to oxidize the methyl group of the substrate to its corresponding —COOH group, forming the carboxylic acid. The carboxylic acid may then be, e.g., further reacted by methods described in the aforementioned '443 application to ultimately yield the novel indole-2-carboxamides disclosed in the '443 application which are useful to treat inflammation and other immune disorders. The activity, methods for testing activities, dosages, dosage forms, methods of administration and background information concerning the novel indole-2-carboxamides disclosed in the '443 application are set forth therein.

In addition, the product carboxylic acids produced by the processes of the present invention, e.g., 2-quinolinecarboxylic acid, 3-quinolinecarboxylic acid, 8-quinolinecarboxylic acid, 3-isoquinolinecarboxylic acid, and 2-indolecarboxylic acid are known in the art and are commonly employed as substitutents on a variety of pharmacologically active compounds. See, for example, "Anthranilic acid derivatives as multidrug resistance modulators," WO98/17648; "Preparation of quinolinecarboxamides and indolecarboxamides as nod DHODH blocking B cell inhibitors," WO99/41239; "Synthesis and evaluation of heterocyclic carboxamides as potential antipsychotic agents," *J. Med. Chem.* (1996), 39(24), 4692–4703; "Preparation of 2-aminopyridinederivatives as nitric oxide synthase inhibitors," WO 00/27842; "Preparation of sandramycin analogs as anticancer agents," WO98/43663; Preparation of azocine peptide derivatives as protease inhibitors," WO00/00706; Preparation of benzooxazolyl piperidines and analogs as rotamase enzyme inhibitors," WO00/05232; and "Acylpiperazinylpyrimidines with pharmacological activity," WO99/05121.

As discussed above, any suitable microorganism, or suitable mutant thereof, may be used in the processes of the present invention. As would be understood by those skilled in the art in light of the present disclosure, the conditions of the subject processes would be chosen depending upon, e.g., the kind of microorganism and the particular preparation thereof. For example, the pH, temperature, component concentrations, and the like, of the, e.g., fermentation medium and organic solvent, as well as the concentrations of the substrate and the inducer (where employed) will be chosen to provide the particular desired result using the selected microorganism.

As discussed earlier, the present invention includes the use of any suitable mutants of any of the suitable microorganisms. In addition, a group of mutants with more desirable properties, e.g., able to oxidize greater amounts of substrate, compared to the parent strain, can also be used in the subject process, and these new strains may be made using known methods including, for example, standard mutagenesis and selection techniques, and recombinant methods including, for example, site-directed mutagenesis.

Standard mutagenesis methods include chemical mutagenesis with N-methyl-N'-nitrosoguanidine (Delic et al. (1970), *Mutat. Res.* 9:167), nitrous acid (Crueger and Crueger (1984), *Biotechnology: A Textbook of Industrial Microbiology*, p. 16, Sinauer Associates, Inc., Sunderland, Mass., USA) and irradiation with ultraviolet light (Thrum (1984), in *Biotechnology of Industrial Antibiotics* (Vandamme, ed.), Marcel Dekker, New York, pp. 373–374).

Selection techniques include simple reisolation of the strain by the selection of an isolated colony, selection of specific colony morphologies and selection for resistance to analogues of components known or thought to be in the biosynthetic pathway of the compound of Formula I (Crueger and Crueger (1984), *Biotechnology: A Textbook of Industrial Microbiology*, p. 24–25, Sinauer Associates, Inc., Sunderland, Mass., USA).

These new strains are used in the subject processes because, for example, they have improved properties relative to their respective parent strains, e.g., they produce more of the product carboxylic acid, they exhibit less unwanted intrinsic degradative activity of substrate and/or product carboxylic acid and/or the intermediate compounds which may be generated in the process of the present invention depending upon, for example, the particular microorganism chosen. In addition, where the mutant is utilized because its use results in more product carboxylic acid, less volume of the culture needs to be grown to obtain the material necessary to generate an amount of product carboxylic acid according to the present process which may result in substantial cost-savings.

As described earlier, any suitable preparation of the microorganism may be used in the processes of the present invention such as, for example, microorganism in growth medium, microorganism washed free of, e.g., fermentation medium, culture broth, and the like, or microorganism immobilized, e.g., in a column, attached to beads, and the like.

Those skilled in the art will understand from the description provided herein how to prepare suitable immobilized intact microorganism such as described, for example, by A. Bauer et al. in the article "Polyvinyl alcohol-immobilized whole-cell preparations for biotransformation of nitriles" published in *Biotechnology Letters*, 18(3): 343–348 (1996).

Preferred intact microorganisms will be those which substantially oxidize the substrate to the product while leaving the product substantially unaltered, e.g., free from intrinsic activity which might degrade or otherwise negatively impact the desired product at any stage of the subject processes.

The microorganisms suitable for use in the subject microbial oxidation may be prepared by any suitable method known to those skilled in the relevant art. An example of a suitable method for the preparation of a microorganism from a commercially purchased stock is provided below. Based upon the present disclosure including the methods provided below, those skilled in the art would understand how to modify any part of these methods, e.g., method of preparing the microorganism, free or immobilized; method of contacting of the substrate with the microorganism; growth medium components and conditions, e.g., temperature, pH and the like; respective concentrations of substrate, inducer (where used); or incubation conditions; to achieve the desired result using any suitable microorganism.

In embodiments of the present invention wherein the microorganism is a fungus, the substrate, namely, 2-methylquinoline, 3-methylisoquinoline, 2-methlindole, or 5-chloro-2-methylindole, can be added in any suitable way (e.g., in a single addition, multiple additions, or continuously), and a preferred concentration range for the total amount of substrate is from about 0.01 g/L to about 2.5 g/L, and a particularly preferred range is from about 0.1 g/L to about 2.0 g/L.

In embodiments of the present invention wherein the microorganism is a bacterium, the substrate, namely, 3-methylisoquinoline, 3-methylquinoline, and 8-methylquinoline, can be added in any suitable way (e.g., in a single addition, multiple additions, or continuously), and a preferred concentration range for the total amount of substrate is from about 0.01 g/L to about 15 g/L, and a particularly preferred range is from about 0.1 g/L to about 15 g/L. In embodiments of the present invention wherein the bacterium is selected from the group consisting of *Pseudomonas putida* ATCC No. 33015, *Pseudomonas putida* ATCC No. 202190 and suitable mutants thereof, a preferred concentration range of substrate is from about 0.1 g/L to about 15 g/L.

In addition, and as discussed earlier, bacterium carrying a TOL plasmid, e.g., *Pseudomonas putida* ATCC No. 33015 or *Pseudomonas putida* ATCC No. 202190, required for the subject oxidation, must be induced. In embodiments of the present invention wherein *Pseudomonas putida* ATCC No. 33015 or *Pseudomonas putida* ATCC No. 202190 is cultivated in a medium in a fermentor, the inducer, is preferably p-xylene, and most preferably benzyl alcohol. In embodiments of the present invention wherein the inducer is p-xylene, its rate of addition is from about 4.5 mmol/L/hour to about 6.5 mmol/L/hour, and a particularly preferred rate of addition is from about 4.9 mmol/L/hour to about 6.1 mm/L/hour.

In embodiments of the present invention wherein the inducer is benzyl alcohol, its rate of addition is from about 0.4 mmol/L/hour to about 5.1 mmol/L/hour, and a particularly preferred rate of addition is from about 3.5 mmol/L/hour to about 5.1 mmol/L/hour.

In embodiments of the present invention wherein *Pseudomonas putida* ATCC No. 33015 or *Pseudomonas putida* ATCC No. 202190 is in a medium in a flask, the inducer, p-xylene, is added continuously in gaseous form to the medium. As would be understood by those skilled in the art from the present disclosure and from the aforementioned articles and patents (e.g., U.S. Pat. No. 5,236,832), the inducer concentration is usually selected so that it is lower than the minimal inhibitory concentration of the enzymes responsible for the oxidation. See also, Claus and Walker, *J. Gen. Microbiol.*, 36:107–122 (1964).

Any suitable method of contacting the substrate with the microorganism may be used in the present invention. The substrate may be contacted with the microorganism in any suitable order. For example, the substrate may be added to a medium, such as a culture broth, comprising the microorganism, free or immobilized, or some combination thereof; or the medium may comprise the substrate and the microorganism may then be added to such medium; or the substrate and the microorganism may be added together to such medium; or either the substrate or the microorganism may be added to a suitable solvent comprising the other; or the substrate may be adsorbed to a resin; and the like. Those skilled in the art will understand from the description provided herein how to modify any part of the subject processes as so desired.

As also discussed above, in an embodiment of the present invention the microorganism is *Absidia repens* ATCC No. 14849. A lyophilized sample of *A. repens* ATCC No. 14849 was deposited by Pfizer, Inc., the owner thereof, with the ATCC under the terms of the Budapest Treaty on Jan. 13, 1999. This newly deposited culture was given the new deposit number of ATCC No. 74481. Hence, in another embodiment of the present invention that the microorganism is *Absidia repens* ATCC No. 74481. All restrictions on the availability to the public of the microorganism culture so deposited will be irrevocably removed upon the issuance of a patent from the specification of the present invention.

Cultures of the fungus *A. repens* ATCC No. 14849 (or *A. repens* ATCC No. 74481) can be obtained from the ATCC, and an example of a suitable method for preparation from such an available stock is provided immediately below. Stock cultures can be prepared from rice cultures such as, for example, as follows: Erlenmeyer flasks (250 mL) containing about 50 g of brown rice and about 20 mL of distilled water are autoclaved at about 121° C. for about 30 min, a suspension of *Absidia repens* ATCC No. 14849 (or *Absidia repens* ATCC No. 74481) vegetative cells, or spores, is prepared by adding either an aliquot of a liquid culture or a swab from a slant culture grown on agar medium to sterile distilled water. Each rice flask is inoculated with about 5 mL of the spore or cell suspension and incubated for about 10 days at about 28° C., at which time the spore stock is prepared by washing the rice culture with about a 0.5% solution of Tween 80 in distilled water, decanting the spore suspension away from the rice, and adding from about 10% to about 20% glycerol. The spore stock is stored at about −70° C.

As would be understood by those skilled in the art for any fungus selected, and as provided specifically hereinafter in the examples, a suitable method for preparing the selected fungus is as follows: the fungus is inoculated from the frozen vegetative cell or spore stock culture such as described above into a flask or a glass tube with a metal closure containing a growth medium (containing an aliquot from a sterile solution which includes Tween 80, glycerol and distilled water) whose composition is described in more detail below. The fermentation is carried out at temperatures ranging from about 22° C. to about 32° C., and preferably at about 29° C., with suitable shaking, preferably from about 200 rpm to about 220 rpm, and most preferably, at about 210 rpm. Where so desired, the pH of the growth medium can be maintained by the use of suitable buffers incorporated into the fermentation medium and/or periodically adjusted by addition of either base or acid as so required. A preferred pH range is from about pH 6 to about pH 7.

Any suitable duration of growth of the microorganism (i.e., fungus or bacterium), contacting of the microorganism with substrate, and incubation of substrate with the microorganism may be used in the present invention. Suitable growth of the microorganism may be achieved, e.g., within about 24 hours, at which time either (a) substrate itself, (b) a suitable aliquot of a solution of the substrate in a suitable, e.g., does not undesirably affect the growth or function of the microorganism, solvent, preferably EtOH or (c) the substrate adsorbed to a resin, may be added to the culture. The incubation may then be continued for, e.g., from about two to about twenty-four days, depending upon, for example, the vessel in which the bioconversion occurs, the medium and conditions, e.g., temperature, pH and agitation, of incubation. The incubation broth may then be extracted using any suitable extraction method, for example, (a) whereby a suitable solvent, such as, for example, EtOAc, methyl isobutylketone, methyl ethylketone, methylene chloride, and the like, preferably, EtOAc, removes the organic components from the incubation broth or (b) by adsorption of the product carboxylic acid, onto a suitable resin, preferably a polymeric adsorbent resin, more preferably a resin selected from those of the tradename Amberlite® (Rohm and Haas), most preferably XAD4 or XAD16 (of the Amberlite resins). After extraction of the incubation broth with a suitable organic solvent and separation of the organic and aqueous phases, the compounds comprising the organic residue may be determined using any suitable method, such as, for example, chromatography. Alternatively, after extraction of product carboxylic acid from the incubation broth using a resin, the product carboxylic acid can be eluted therefrom using a suitable solvent, preferably EtOAc or MeOH, and then crystallized from the, e.g., EtOAc, using, for example, EtOAc and MeOH.

Any suitable growth medium may be used in the process of the present invention, and the suitable growth medium will contain a source or sources of assimilable carbon, assimilable nitrogen and inorganic salts containing essential minerals. In general, many carbohydrates such as, for example, glucose, maltose, mannose, sucrose, starch, glycerin, millet jelly, molasses, soy bean, and the like, can be used as sources of assimilable carbon. Sources of assimilable nitrogen include, for example, materials such as yeast and casein hydrolysates, primary yeast, yeast extracts, cottonseed flour, soybean solids, wheat germ, meat extracts, peptone, cornsteep liquor, cornsteep solids, and ammonium salts. Suitable inorganic salt nutrients for use in the culture medium of the present invention include, for example, the customary salts containing sodium, iron, magnesium, potassium, cobalt, phosphate, and the like.

More particularly, components of growth media suitable for use in the present invention where the microorganism is a fungus include, for example, cornsteep liquor, cornsteep solids, Pharmamedia® and malt extract. Cornsteep liquor medium is prepared with about 40 g/L cornsteep liquor and about 20 g/L dextrose, and adjusted to about pH 4.85 before sterilization. Cornsteep solids medium is prepared with from about 20 g/L to about 40 g/L cornsteep solids and about 20 g/L dextrose, and adjusted to about pH 4.85 before sterilization. Another suitable medium for use in the processes of the present invention is prepared with about 20 g/L Pharmamedia® and about 20 g/L dextrose, and adjusted to about pH 7.2 before sterilization. Malt extract medium is prepared with about 10 g/L malt extract, about 10 g/L dextrose, about 5 g/L peptone, and about 2 g/L yeast extract, and adjusted to about pH 7 before sterilization. Another suitable medium for use in the processes of the present invention is prepared with about 20 g/L of dextrose, about 5 g/L of nutrisoy flour, about 5 g/L of yeast extract, about 5 g/L of NaCl and about 5 g/L of $K_2HPO_4$, with the pH adjusted to about pH 7.0 with $H_2SO_4$ before sterilization. A particularly preferred growth medium for the fungi suitable for the present process is the aforementioned cornsteep solids medium.

As discussed above, it is particularly preferred in certain embodiments of the present invention that the microorganism is Pseudomonas putida ATCC No. 33015. As also discussed above, a lyophilized sample of Pseudomonas putida ATCC No. 33015 was deposited by Pfizer, Inc., the owner thereof, with the ATCC under the terms of the Budapest Treaty on Jan. 13, 1999. This newly deposited culture was given the new deposit number of ATCC No. 202190. Hence, it is also preferred in the present invention that the microorganism is Pseudomonas putida ATCC No. 202190. All restrictions on the availability to the public of the microorganism culture so deposited will be irrevocably removed upon the issuance of a patent from the specification of the present invention.

In addition, growth media suitable for use in the present invention where the microorganism is a bacterium include any suitable known media, e.g., Nutrient Broth (about 32 g/L, Becton Dickinson Microbiology Systems) and glycerol (about 5 g/L). Another suitable medium for use in the processes of the present invention wherein the microorganism is a bacterium is prepared from about 6 g/L $Na_2HPO_4$, 3 g/l $KH_2PO_4$, 1 g/L $NH_4Cl$, 0.5 g/L NaCl, 1 mL/L of 1M $MgSO_4$, 1 m/L/L of 0.1M $CaCl_2$, 15 mL/L of FeEDTA, and 1 mL/L of a trace elements solution. The trace elements solution is prepared with about 10 g/L $Na_2EDTA.2H_2O$, 9 g/L $ZnSO_4.7H_2O$ 4 g/L $MnCl_2.4H_2O$, 2.7 g/L $H_3BO_3$, 1.8 g/L $CoCl_2.6H_2O$, 1.5 g/L $CuCl_2.2H_2O$, 0.18 g/L $NiCl_2.6H_2O$, and 0.2 g/L $Na_2MoO_4.2H_2O$. The FeEDTA solution is prepared with 5 g/L $Na_2EDTA.2H_2O$, and 2 g/L $FeSO_4.7H_2O$.

As would be understood by those skilled in the art for any bacterium selected, and as provided specifically hereinafter in the examples for Pseudomonas putida ATCC No. 33015, a suitable method for preparing the selected bacterium is as follows: the bacteria is inoculated from a frozen stock culture prepared as is known in the art (about a 17% glycerol stock) into a flask or a glass tube with a metal closure or a fermentor containing a growth medium (containing an aliquot from a sterile solution which includes Tween 80, glycerol and distilled water) whose composition is described in more detail below. The fermentation is carried out at temperatures ranging from about 20° C. to about 40° C., and preferably at temperatures ranging from about 25° C. to about 32° C., with suitable shaking, preferably from about 200 rpm to about 220 rpm, and most preferably, at about 210 rpm. Where so desired, the pH of the growth medium can be maintained by the use of suitable buffers incorporated into the fermentation medium and/or periodically adjusted by addition of either base or acid as so required. A preferred inoculum is from about 1% to about 20% v/v (inoculum/medium). A preferred pH range is from about pH 6 to about pH 8.

It should be noted that reference to particular buffers, media, reagents, contacting or culture conditions, amount of substrate, amount of inducer where used, and the like, in any part of the present disclosure is not intended to be limiting, but should be read to include all such related materials that those of ordinary skill in the art would recognize as being of interest or value in the particular context in which the discussion herein is presented. For example, it is often possible to substitute one buffer system or culture medium for another, such that a different but known way is used to achieve the same goals as those to which the use of a suggested method, material or composition is directed. Moreover, it should be understood that the present invention includes the scaling-up of the subject process for commercial purposes.

The subject microbial oxidation further optionally comprises the isolation of the desired product carboxylic acid. The product carboxylic acid may be isolated as described below from the medium in which the novel microbial oxidation process was performed and, more specifically, from any intermediate compounds which may have been produced but not completely converted to the product carboxylic acid depending upon, e.g., the microorganism selected and the conditions of incubation.

Any suitable methods for isolating and/or purifying any of the intermediates or the desired product of the subject process may be used in the present invention including filtration, extraction, crystallization, column chromatography, thin-layer chromatography, preparative low pressure liquid chromatography, HPLC, resin adsorption, or any suitable combination of such methods.

The detailed examples provided below show that a range of microorganisms, specifically, fungi and bacteria, oxidize certain bicyclic heteroaromatic compounds to yield their respective corresponding carboxylic acids which may then be separated from any unwanted unaltered substrate, or any intermediate compounds, and further reacted according to methods well known in the art to yield, e.g., the compounds of the '443 application, or the compounds described in the documents mentioned hereinabove that describe use of the product carboxylic acids as common substituents of various pharmaceutically active compounds useful in the treatment of a variety of diseases or conditions.

Although the present disclosure is primarily directed to the use of intact microorganisms in the subject processes, those skilled in the art would understand that the subject microbial processes may be accomplished by suitable preparations thereof, e.g., broken and dehydrated cell preparations, extracted materials comprising the microbial enzymes capable of accomplishing the subject oxidations, or the enzymes themselves, together with any necessary cofactors, and the like.

The present invention is illustrated by the following examples. The foregoing and following description of the present invention and the various embodiments are not intended to be limiting of the invention but rather are illustrative thereof. Hence, it will be understood that the invention is not limited to the specific details of these examples.

EXAMPLE I

Screen for Microbial Conversion of Quinaldine, 3-Methylisoquinoline, 2-Methylindole, and 5-Chloro-2-Methylindole A. Bioconversion Using Various Fungi and a Bacterium Cells of various microorganisms were grown in 16×125 mm glass tubes containing 2.5 mL of sterile growth medium. The growth medium contained about 20 g/L of dextrose, about 5 g/L of nutrisoy flour, about 5 g/L of yeast extract, about 5 g/L of NaCl and about 5 g/L of $K_2HPO_4$, with the pH adjusted to about pH 7.0 with $H_2SO_4$ before sterilization. Twelve tubes were inoculated with spores or vegetative cells (about 1% v/v of spore or vegetative cell stock culture) of each microorganism stored as frozen glycerol suspensions, and incubated at about 29° C. with agitation (210 rpm) on a rotary shaker. After about 48 hours, 0.05 mL of 10 mg/mL solutions of quinaldine, 3-methylisoquinoline, 2-methylindole, and 5-chloro-2-methylindole in DMSO were separately added to three tubes of each microorganism. After about 4, 7, and 10 days incubation, the contents of tubes from each microorganism, and for each substrate, were extracted. The contents of each tube culture were extracted with an equal volume of EtOAc (neat): the EtOAc was added, the tube culture was vortexed and then centrifuged at about 2,000 rpm (IEC Centrifuge). The EtOAc layer was removed and dried down under nitrogen in a water bath at about 50° C.

B. Yields of Product Carboxylic Acids as Determined by Reverse-Phase HPLC

Each of the extracts, prepared as described above, was resuspended in about one mL of ACN:water (1:9, v/v), and about 20 uL of each resuspended extract was analyzed by injection onto an HPLC column: Inertsil® C8 HPLC column (4.6×250 mm, Column Engineering, Inc.). The compounds contained within each injected resuspended extract were separated isocratically at about 1.0 mL per minute in a mobile phase consisting of mixtures of ACN and 0.05% aqueous TFA. The proportions of ACN and 0.05% aqueous TFA used for analysis of the extracts obtained from the tubes to which quinaldine, 3-methylisoquinoline, 2-methylindole, and 5-chloro-2-methylindole had been added were 7:93, 5:95, 45:55, and 50:50, respectively. The yields of quinaldic acid, 3-isoquinolinecarboxylic acid, 2-indolecarboxylic acid, and 5-chloro-2-indolecarboxylic acid were determined by HPLC.

For quinaldic acid: *Cunninghamella echinulata* ATCC Nos. 9244 (38%), 8688a (38%), 26269 (38%), 8983 (37%), 10028b (36%, 9245 (36%), and 36112 (34%), *Cunninghamella homothallica* ATCC No. 16161 (28%), *Alternaria solani* ATCC No. 11078 (28%), *Penicillium glabrum* ATCC No. 11080 (27%), and *Diplodia gossypina* ATCC No. 20575 (22%).

For 3-isoquinolinecarboxylic acid: *Cunninghamella echinulata* ATCC Nos. 8688a (25%), *Alternaria solani* ATCC No. 11078 (26%), *Diplodia gossypina* ATCC No. 20575 (28%), *Aspergillus tamarii* ATCC No. 16865 (44%), and *Glomerella langenaria* ATCC No. 14724.

For 2-indolecarboxylic acid: *Rhodococcus rhodochrous* ATCC No. 19067 (25%).

For 5-chloro-2-indolecarboxylic acid: *Rhodococcus rhodochrous* ATCC No. 19067 (65%).

As illustrated by the data provided hereinabove, for each substrate, HPLC analysis shows that the subject microbial processes result in the production of the respective carboxylic acids.

Accordingly, the inclusion of a suitable intact microorganism results in the oxidation of the bicyclic aromatic substrates to their corresponding carboxylic acids.

EXAMPLE II

Oxidation of 2-Methylquinoxaline, 3-Methylquinoline, 8-Methylquinoline, and 3-Methylisoquinoline Using *Pseudomonas putida* ATCC NO. 33015 Induced With Benzyl Alcohol A. Bioconversion Using the Bacterium *Pseudonomoas putida* ATCC No. 33015.

*Pseudomonas putida* ATCC No. 33015 was grown in a fermentor with about 8 L of a medium that was prepared with 6 g/L $Na_2HPO_4$, 3 g/L $KH_2PO_4$, 1 g/L $NH_4Cl$, 0.5 g/L NaCl, 1 ml/L 1 M $MgSO_4$, 1 m/L/L 0.1 M $CaCl_2$, 15 mL/L FeEDTA (prepared with 5 g/L $Na_2EDTA2H_2O$ and 2 g/L $FeSO_4$, $7H_2O$) and 1 mL/L of a trace elements solution (prepared with 10 g/L $Na_2EDTA2H_2O$, 9 g/L $ZnSO_47H_2O$, 4 g/L $MnCl_24H_2O$, 2.7 g/L $H_3BO_3$, 1.8 g/L $CoCl_26H_2O$, 1.5 g/L $CuCl_2.2H_2O$, 0.18 g/L $NiCl_2.6H_2O$, and 0.2 g/L $Na_2MoO_42H_2O$). The fermentor was inoculated with one culture of *Pseudomonas putida* grown in a 2.8 L Fernbach flask containing about 400 mL of the immediately above-described medium. This flask culture was inoculated with about 1.8 ml of a spore stock of *Pseudomonas putida* ATCC 33015 followed by addition of 0.4 mL of benzyl alcohol. The flask culture was incubated at about 29° C. for 24 hours with shaking at about 210 rpm. The fermentor culture was incubated at 29° C. with aeration at 8 Lpm, and pH controlled to 7.0 by the addition of NaOH. Agitation of the fermentor culture was maintained at 600 rpm. After inoculation of the fermentor with the flask culture, benzyl alcohol was added to the fermentor by pump starting at a rate of 0.64 mmol/Uh. After 22 h, the benzyl alcohol addition rate was increased to 1.13 mmol/Uh. Further increases in the benzyl alcohol addition rate to 2.13 and 2.90 mmol/Uh were made at 30 h and 47 h, respectively. Ammonium chloride (10 g) was added to the fermentor about 31 h after inoculation. At about 53 h after inoculation, incubation medium was removed from the fermentor and 200 ml aliquots were placed into eight 1 L erlenmeyer flasks. The eight flasks were divided into four groups and the flasks in each group treated with 0.1 g of one of the following compounds: 2-methylquinoxaline, 3-methylquinoline, 8-methylquinoline, and 3-methylisoquinoline. The flasks were then incubated at 29° C. with shaking at 210 rpm. At about 45 h after addition of the compounds, samples of the incubation medium were removed from the flasks, centrifuged to remove the cells, and diluted with MeOH.

B. Yields of Product Carboxylic Acids as Determined by Reverse-Phase HPLC

The diluted samples from step A. were analyzed by HPLC. The samples taken from the flasks treated with 2-methylquinoxaline and were analyzed as described in the examples section of the '548 application. The samples taken from the flasks treated with either 3-methylquinoline or 3-methylisoquinoline were analyzed on a Symmetry® C18 HPLC column (3.9×150 mm) eluted at about 1.0 mL/min with a mobile phase consisting of a mixture of ACN:0.05% aqueous TFA (1:9, v/v). Samples taken from the flasks treated with 8-methylquinoline were analyzed on a Discovery™ RPamideC16 HPLC column (4.6×150 mm) eluted at about 1.0 mL/min with a mobile phase consisting of a mixture of ACN:0.05% aqueous TFA (1:9, v/v).

The % yield of the "control," namely, 2-quinoxalinecarboxylic acid (see the '548 application), was about 106%. The % yield of 3-quinolinecarboxylic acid was about 9%. The % yield of 8-quinolinecarboxylic acid was about 17%. The % yield of 3-isoquinolinecarboxylic acid was 21%.

As illustrated by these data, the contacting of *Pseudomonas putida* ATCC No. 33015 with each of the four substrates, i.e., one control and three tests, resulted in the production of an amount of the desired corresponding carboxylic acids. Accordingly, the inclusion of a suitable intact microorganism, i.e., *Pseudomonas putida* ATCC No. 33015, results in the oxidation of these bicyclic aromatic substrates to their corresponding carboxylic acids.

What is claimed is:

1. A process for the microbial oxidation of the compound of Formula II

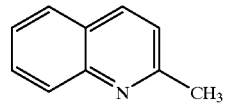

to the compound of Formula I

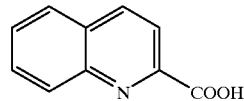

which comprises:
  contacting said compound of Formula II with a microorganism capable of accomplishing the oxidation of the methyl group of the compound of Formula II to the carboxyl group of the compound of Formula I, and
  incubating the resultant mixture to yield an amount of the compound of Formula I.

2. The process as defined in claim 1 wherein said microorganism is selected from the group consisting of *Cunninghamella echinulata* ATCC No. 9244, *Cunninghamella echinulata* ATCC No. 8688a, *Cunninghamella echinulata* ATCC No. 26269, *Cunninghamella echinulata* ATCC No. 8983, *Cunninghamella echinulata* ATCC No. 10028b, *Cunninghamella echinulata* ATCC No. 9245, *Cunninghamella echinulata* ATCC No. 36112, *Cunninghamella homothallica* ATCC No. 16161, *Alternaria solani* ATCC No. 11078, *Penicillium glabrum* ATCC No. 11080, *Diplodia gossypina* ATCC No. 20575, *Absidia repens* ATCC No. 14849, *Absidia repens* ATCC No. 74481, *Aspergillus tamarii* ATCC No. 16865, and *Glomerella lagenaria* ATCC No. 14724.

3. The process as defined in claim 2 wherein said microorganism is selected from the group consisting of *Cunninghamella echinulata* ATCC No. 9244, *Cunninghamella echinulata* ATCC No. 8688a, *Cunninghamella echinulata* ATCC No. 26269, *Cunninghamella echinulata* ATCC No. 8983, *Cunninghamella echinulata* ATCC No. 10028b, *Cunninghamella echinulata* ATCC No. 9245, *Cunninghamella echinulata* ATCC No. 36112, *Cunninghamella echinulata* ATCC No. 16161, *Alternaria solani* ATCC No. 11078, *Penicillium glabrum* ATCC No. 11080, and *Diplodia gossypina* ATCC No. 20575.

4. The process as defined in claim 1 wherein said microorganism is an intact microorganism, and further comprising isolating said compound of Formula I by extraction of said mixture with an organic solvent, and subjecting said extraction to chromatography.

* * * * *